US00PP24935P2

(12) United States Plant Patent
Dümmen

(10) Patent No.: US PP24,935 P2
(45) Date of Patent: Sep. 30, 2014

(54) ***MANDEVILLA* PLANT NAMED 'DUEMALACHE'**

(50) Latin Name: *Mandevilla sanderi*
Varietal Denomination: Duemalache

(71) Applicant: Tobias Dümmen, Rheinberg (DE)

(72) Inventor: Tobias Dümmen, Rheinberg (DE)

(73) Assignee: Dümmen Group B.V., De Lier (NL)

( * ) Notice: Subject to any disclaimer, the term of this patent is extended or adjusted under 35 U.S.C. 154(b) by 106 days.

(21) Appl. No.: 13/694,135

(22) Filed: Oct. 31, 2012

(51) Int. Cl.
*A01H 5/00* (2006.01)

(52) U.S. Cl.
USPC ..... Plt./232

(58) Field of Classification Search
USPC ..... Plt./232
See application file for complete search history.

*Primary Examiner* — Wendy C Haas
(74) *Attorney, Agent, or Firm* — C. A. Whealy

(57) ABSTRACT

A new and distinct cultivar of *Mandevilla* plant named 'Duemalache', characterized by its upright and outwardly spreading plant habit; vigorous growth habit; freely branching habit; early and freely flowering habit; and red purple-colored flowers.

1 Drawing Sheet

Botanical designation: *Mandevilla sanderi.*
Cultivar denomination: 'DUEMALACHE'.

BACKGROUND OF THE INVENTION

The present invention relates to a new and distinct cultivar of *Mandevilla* plant, botanically known as *Mandevilla sanderi* and hereinafter referred to by the name 'Duemalache'.

The new *Mandevilla* plant is a product of a planned breeding program conducted by the Inventor in Rheinberg, Germany. The objective of the breeding program is to create new freely branching and early flowering *Mandevilla* plants with numerous attractive flowers.

The new *Mandevilla* plant originated from a cross-pollination made by the Inventor in Rheinberg, Germany in July, 2007 of a proprietary selection of *Mandevilla sanderi* identified as code number F-04-08-5, not patented, as the female, or seed parent with a proprietary selection of *Mandevilla sanderi* identified as code number F-19-16, not patented, as the male, or pollen, parent. The new *Mandevilla* plant was discovered and selected by the Inventor as a single flowering plant from within the progeny of the stated cross-pollination in a controlled greenhouse environment in Rheinberg, Germany in May, 2011.

Asexual reproduction of the new *Mandevilla* plant by cuttings in Rheinberg, Germany since July, 2011 has shown that the unique features of this new *Mandevilla* plant are stable and reproduced true to type in successive generations.

SUMMARY OF THE INVENTION

Plants of the new *Mandevilla* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Duemalache'. These characteristics in combination distinguish 'Duemalache' as a new and distinct *Mandevilla* plant:

1. Upright and outwardly spreading plant habit.
2. Vigorous growth habit.
3. Freely branching habit.
4. Early and freely flowering habit.
5. Red purple-colored flowers.
6. Good garden performance.

Plants of the new *Mandevilla* can be compared to plants of the female parent selection. Plants of the new *Mandevilla* differ primarily from plants of the female parent selection in plant habit as plants of the new *Mandevilla* are more compact than plants of the female parent selection.

Plants of the new *Mandevilla* can be compared to plants of the male parent selection. Plants of the new *Mandevilla* differ primarily from plants of the male parent selection in flower color as plants of the male parent selection have pink-colored flowers.

Plants of the new *Mandevilla* can be compared to plants of *Mandevilla atroviolacea*×(*Mandevilla amabilis*×*boliviensis*) 'Sunmandecrim', disclosed in U.S. Plant Pat. No. 15,539. In side-by-side comparisons conducted in Rheinberg, Germany, plants of the new *Mandevilla* differed primarily from plants of 'Sunmandecrim' in the following characteristics:

1. Plants of the new *Mandevilla* were more compact than plants of 'Sunmandecrim'.
2. Plants of the new *Mandevilla* had shorter internodes than plants of 'Sunmandecrim'.
3. Plants of the new *Mandevilla* and 'Sunmandecrim' differed in flower color as plants of 'Sunmandecrim' had lighter red-colored flowers.

BRIEF DESCRIPTION OF THE PHOTOGRAPH

The accompanying colored photograph illustrates the overall appearance of the new *Mandevilla* plant showing the colors as true as it is reasonably possible to obtain in colored reproductions of this type. Colors in the photograph may differ slightly from the color values cited in the following detailed botanical description which accurately describe the actual colors of the new *Mandevilla* plant. The photograph comprises a side perspective view of a typical flowering plant of 'Duemalache' grown in a container.

DETAILED BOTANICAL DESCRIPTION

The aforementioned photograph and following observations, measurements and values describe plants grown in 10.5-cm containers during the summer in a glass-covered greenhouse in Rheinberg, Germany and under cultural practices typical of commercial *Mandevilla* production. During the production of the plants, day and night temperatures averaged 18° C. and light levels averaged 4,500 lux. Plants were pinched one time and were 20 weeks old when the photograph and description were taken. In the following description, color references are made to The Royal Horticultural Society Colour Chart, 1995 Edition, except where general terms of ordinary dictionary significance are used.

Botanical classification: *Mandevilla sanderi* 'Duemalache'.

Parentage:

*Female, or seed, parent*.—Proprietary selection of *Mandevilla sanderi* identified as code number F-04-08-5, not patented.

*Male, or pollen, parent*.—Proprietary selection of *Mandevilla sanderi* identified as code number F-19-16, not patented.

Propagation:

*Type*.—By cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; white in color.

*Rooting habit*.—Freely branching; dense.

Plant description:

*Plant and growth habit*.—Upright and outwardly spreading; vigorous growth habit; moderate growth rate.

*Plant height*.—About 80 cm.

*Plant diameter*.—About 35 cm.

*Lateral branch description*.—Branching habit: Freely branching habit with about eleven lateral branches developing per plant; pinching enhances lateral branch development. Length: About 20 cm. Diameter: About 2 mm. Internode length: About 3 cm. Strength: Strong; flexible. Texture: Smooth, glabrous. Color: Close to 144A tinged with close to 200C.

Foliage description:

*Arrangement*.—Opposite, simple.

*Length*.—About 6.8 cm.

*Width*.—About 3.6 cm.

*Shape*.—Elliptical.

*Apex*.—Apiculate.

*Base*.—Rounded or truncate.

*Margin*.—Entire.

*Texture, upper and lower surfaces*.—Smooth, glabrous.

*Venation pattern*.—Pinnate, arcuate.

*Color*.—Developing leaves, upper surface: Close to 144A. Developing leaves, lower surface: Close to 144B. Fully expanded leaves, upper surface: Close to 139A; venation, close to 144C. Fully expanded leaves, lower surface: Close to 146A; venation, close to 144D.

*Petioles*.—Length: About 1.3 cm. Diameter: About 2 mm. Texture, upper and lower surfaces: Smooth, glabrous. Color, upper surface: Close to 139A. Color, lower surface: Close to 138B.

Flower description:

*Flower type and habit*.—Salverform flowers alternately arranged in terminal and axillary racemose clusters with about five to six flowers per cluster, freely flowering habit with about 80 to 90 flowers developing per plant; flowers face upright to somewhat outwardly.

*Natural flowering season*.—Early flowering habit and long flowering period, plants begin flowering about nine weeks after planting and flower continuously throughout the summer in Germany.

*Flower longevity on the plant*.—About three to five days; flowers persistent.

*Fragrance*.—None detected.

*Flowers*.—Appearance: Salverform with five-parted fused corolla; flowers roughly star-shaped. Diameter: About 7.5 cm. Depth (length): About 4.1 cm. Throat diameter: About 2 cm. Tube length: About 3.5 cm. Tube diameter at the base: About 4.5 mm.

*Flower buds*.—Height: About 3.7 cm. Diameter: About 5.7 mm. Shape: Elongated oblong, spindle-shaped. Color: Close to 154D and 54A.

*Corolla*.—Arrangement and appearance: Single whorl of five petals; petals not imbricate. Petal lobe length: About 3.4 cm. Petal lobe width: About 2.7 cm. Petal lobe shape: Roughly spatulate. Petal apex: Apiculate. Petal margin: Entire. Petal texture, upper and lower surfaces: Smooth, glabrous. Throat texture: Smooth, glabrous. Tube texture: Smooth, glabrous. Color: Petal lobe, when opening and fully opened, upper surface: Close to 57A; venation, close to 57A; color becoming closer 58B with development. Petal lobe, when opening and fully opened, lower surface: Close to 57B; venation, close to 57B. Throat: Close to 30B; venation, close to 14A. Tube: Close to 59C; venation, close to 144B.

*Sepals*.—Arrangement and appearance: Single whorl of five sepals; sepals not imbricate. Length: About 7.8 mm. Width: About 2 mm. Shape: Ligulate. Apex: Acuminate. Margin: Entire. Texture, upper and lower surfaces: Smooth, glabrous. Color, upper and lower surfaces: Close to 145B.

*Peduncles*.—Length: About 6 cm. Diameter: About 2 mm. Aspect: About 45° from stem axis. Texture: Smooth, glabrous. Strength: Strong, flexible. Color: Close to 154C.

*Pedicels*.—Length: About 2.1 cm. Diameter: About 1 mm. Aspect: About 45° from stem axis. Texture: Smooth, glabrous. Strength: Strong, flexible. Color: Close to 154C.

*Reproductive organs*.—Stamens: Quantity per flower: Typically five. Anther length: About 0.5 mm. Anther shape: Elongated oblong. Anther color: Close to 8B. Pollen amount: Moderate. Pollen color: Close to 3C. Pistils: Quantity per flower: Typically one. Pistil length: About 3.6 cm. Stigma shape: Star-shaped; five-lobed. Stigma color: Close to 138B. Style length: About 2.3 cm. Style color: Close to 1D. Ovary color: Close to 1D.

*Seeds and fruits*.—Seed and fruit production has not been observed on plants of the new *Mandevilla*.

Disease & pest resistance: Plants of the new *Mandevilla* have not been noted to be resistant to pathogens and pests common to *Mandevilla* plants.

Garden performance: Plants of the new *Mandevilla* have been observed to have good garden performance and to tolerate rain, wind, full sunlight and temperatures from about 5° C. to about 40° C.

It is claimed:

1. A new and distinct *Mandevilla* plant named 'Duemalache' as illustrated and described.

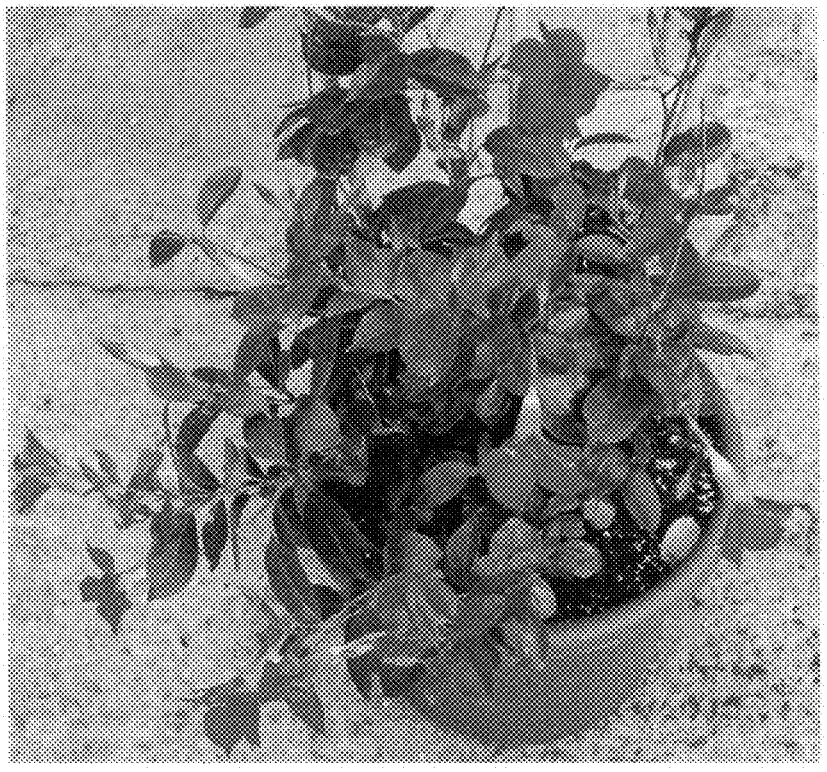

* * * * *